United States Patent [19]

Strickler

[11] 4,163,866
[45] Aug. 7, 1979

[54] PROCESS FOR THE PREPARATION OF A BICYCLIC ALCOHOL

[75] Inventor: Hugo Strickler, Dardagny, Switzerland

[73] Assignee: Firmenich SA, Geneva, Switzerland

[21] Appl. No.: 814,860

[22] Filed: Jul. 12, 1977

[30] Foreign Application Priority Data

Jul. 28, 1976 [CH] Switzerland .......................... 9634/76

[51] Int. Cl.$^2$ ...................... C07C 29/00; C07C 33/02
[52] U.S. Cl. ................................................. 568/819
[58] Field of Search ..................... 260/617 F; 568/819

[56] References Cited

U.S. PATENT DOCUMENTS 3,890,395  6/1975  Jeger et al. ..................... 260/617 F
3,928,456  12/1975  Kovats et al. .................... 260/617 F Primary Examiner—Norman Morgenstern
Attorney, Agent, or Firm—Pennie & Edmonds

[57] ABSTRACT

α-Ambrinol, a bicyclic alcohol of formula

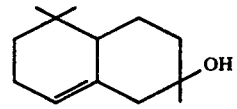

is prepared by a novel process starting from β-ionone via cyclization followed by catalytic reduction.

4 Claims, No Drawings

PROCESS FOR THE PREPARATION OF A BICYCLIC ALCOHOL

THE INVENTION

The present invention relates to a process for the preparation of α-ambrinol which process comprises the steps of (a) subjecting β-ionone to a thermal treatment to give a dehydroambrinol of formula

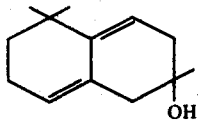

(b) catalytically hydrogenating the said dehydroambrinol.

BACKGROUND OF THE INVENTION

Ambrinols belong to the class of decaline derivatives of generic formula

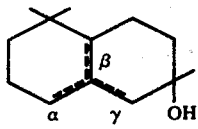

possessing a double bond in position α, β or γ as indicated by the dotted lines.

They possess interesting odoriferous properties [Arno Müller, International Riechstoff-Kodex, Dr. A. Hüthig Verlag, Heidelberg, West-Germany] and consequently have been used advantageously in the manufacture of perfume compositions wherein they develop an olfactive note of amber type; however, in despite of their interest, their utilization sofar has not been extensive. This was eminently due to the poor availability of this class of compounds, the known synthesis for their preparation being rather uneconomical [see e.g. Helv. Chim. Acta, 42, 2233 (1959)]. It is not surprising therefore to observe the constant effort displayed by the whole industry in an attempt to achieve a more economical process for their preparation. The present invention provides an original and useful solution to this problem. Indeed, the process of the invention has the advantage of using, as starting materials, cheaply available products and of enabling the preparation of α-ambrinol with a defined preferential steric arrangement, the OH group being in the axial position [see. G. Ohloff, Chemie der Geruchs- und Geschmacksstoffe, in Fortschritte der chemischen Forschung, vol. 12, page 188 (1969)].

PREFERRED EMBODIMENTS OF THE INVENTION

The thermal treatment of β-ionone in accordance with the process of the invention is preferentially carried out on the said product in its vapour phase by means of a reactor comprising a metallic coil suitably kept at the desired temperature within a thermostatic enclosure. The vapours of β-ionone are preferably mixed with an inert gas, such as e.g. argon or nitrogen, and the obtained mixture is introduced in the reactor at various flow rates. Tje said flow rate depends of course on the quantity of β-ionone which has to be subjected to thermolysis, as well as on the specific parameters which have been chosen as a function of the reactor features.

The temperature at which the thermal treatment is carried out can vary within a broad range. Typically, it is of between about 300° and 500° C., more preferably, it is of about 400° and 450° C. According to a preferred embodiment of the invention, the vapours are collected after thermolysis by means of a set of cooling traps, whereupon the condensate thus obtained gives dehydroambrinol by fractional distillation.

The second step of the process of the invention, viz. the catalytic hydrogenation of the obtained carbinol, can be effected in the presence of a metal catalyst such as for instance Raney nickel, in an alcoholic medium, preferably in the presence of traces of water. It has to be understood, however, that the catalytic hydrogenation can be carried out in the presence of those catalysts which are commonly used in the art to promote the conversion of ethylenic double bonds into saturated ones.

The usual treatments of separation and purification enable the isolation of the desired α-ambrinol with good yields.

The process of the invention is illustrated by the following reaction scheme:

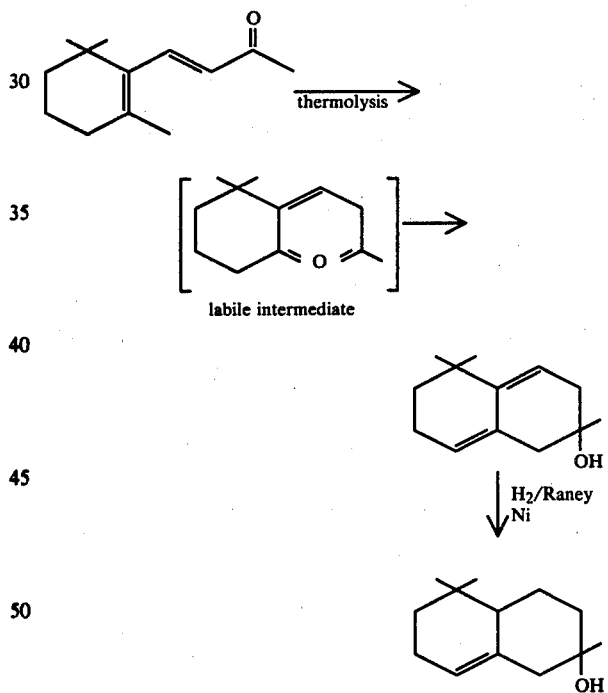

The invention is better illustrated by but not limited to the following example wherein the temperatures are indicated in degrees centigrade and the abbreviations have the meaning common in the art.

EXAMPLE (a) 14.4 kg of β-ionone have been introduced portionwise within 24 h into a metallic coil kept in a thermostatic oven at 430°. Heating was realized by means of hot air and the coil had a total length of 252 cm and a inner section of 39.5 mm.

The flow rate of the vapours of β-ionone was kept constant whilst nitrogen, chosen as carrier gas, was introduced at a flow rate of 40 l/min. At the extremity of the coil, the vapours of β-ionone, after themolysis, were condensed by means of two refrigerators. It was thus possible to obtain a condensate containing 27% of dehydroambrinol in admixture with 24% of ionene and 26% of starting β-ionone.

Dehydroambrinol was separated from the other constituents by fractional distillation at 0.02 Torr pressure using a Sulzer type column of 9 m length. The product had $n_D^{20} = 1.5269$ and $d_4^{20} = 1.004$.

IR: 3370, 3045, 1710, 1666, 1640, 1615, 810, 792 and 780 cm$^{-1}$;

NMR: 1.02 (3H, s); 1.06 (3H, s); 1.16 (3H, s); 1.3–1.6 (2H); 1.8; 2.21 (6H); 5.45 (2H, m) δ ppm;

MS: M$^+$ = 1.92 (45).

(b) 6.5 kg of the thus obtained dehydroambrinol were dissolved in 58.5 kg methanol and admixed with 700 g of Raney nickel previously moistured with distilled water. The mixture was subjected to hydrogenation at room temperature. The total absorption of hydrogen was of 800 l.

After filtration and evaporation, a fractional distillation of the residue gave a fraction of ambrinols containing a major amount of α-ambrinol admixed with minor amounts of α-ambrinol.

IR: 3440, 1668, 994, 910, 876, 800, 792, 746, 725 cm$^{-1}$;

NMR: 0.84 (3H, s); 0.89 (3H, s); 1.11 (3H, s); 1.1–1.9 (9H); 2.00 (3H); 5.34 (1H, m) δ ppm;

MS: M$^+$ = 194 (6).

What I claim is:

1. Process for the preparation of α-ambrinol which comprises the steps of:
    (a) subjecting β-ionone to a thermal treatment at a temperature of between about 300° to 500° C. to give a dehydroambrinol of formula

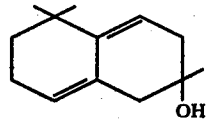

(b) subsequently catalytically hydrogenating the said dehydroambrinol to form α-ambrinol.

2. Process according to claim 1, wherein the catalytic hydrogenation is effected in the presence of Raney nickel in an aqueous alcoholic medium.

3. Process according to claim 1, wherein α-ambrinol is separated after hydrogenation from the other constituents of the obtained reaction mixture by means of fractional distillation.

4. Process according to claim 1 wherein the dehydroambrinol formed by thermal treatment of β-ionone is isolated after thermolysis.

* * * * *